United States Patent
Heyl-Frank et al.

(10) Patent No.: US 7,026,507 B2
(45) Date of Patent: Apr. 11, 2006

(54) METHOD FOR THE PRODUCTION OF SOLID FORMULATIONS OF SODIUM 3-HYDROXY-3-METHYLBUTYRATE

(75) Inventors: Brigitta Heyl-Frank, Schweiz (CH); Heike Irle, Schweiz (CH); Daniel Pianzola, Schweiz (CH); Uwe Zacher, Schweiz (CH); Barry Jackson, Schweiz (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 10/478,054

(22) PCT Filed: May 17, 2002

(86) PCT No.: PCT/EP02/05435

§ 371 (c)(1),
(2), (4) Date: Nov. 18, 2003

(87) PCT Pub. No.: WO02/094255

PCT Pub. Date: Nov. 28, 2002

(65) Prior Publication Data

US 2004/0143136 A1   Jul. 22, 2004

(30) Foreign Application Priority Data

May 18, 2001 (EP) .................... 01112236

(51) Int. Cl.
*C07C 51/42* (2006.01)

(52) U.S. Cl. ....................... 562/580; 562/579
(58) Field of Classification Search ............. 562/512, 562/606, 579
See application file for complete search history.

(56) References Cited

U.S. PATENT DOCUMENTS

| 5,348,979 | A | | 9/1994 | Nissen et al. |
| 5,360,613 | A | * | 11/1994 | Nissen ........................ 424/439 |
| 6,090,978 | A | | 7/2000 | McCoy et al. |
| 6,248,922 | B1 | | 6/2001 | McCoy et al. |
| 6,384,242 | B1 | * | 5/2002 | Fankhauser et al. ........ 549/328 |

FOREIGN PATENT DOCUMENTS

| WO | 94/06417 | 3/1994 |
| WO | 94/14429 | 7/1994 |
| WO | 98/34897 | 8/1998 |

OTHER PUBLICATIONS

Nissen, S., et al., The Journal of Nutrition, vol. 130, No. 8, (2000), pp. 1937-1945.

* cited by examiner

*Primary Examiner*—Johann Richter
*Assistant Examiner*—Karl Puttlitz
(74) *Attorney, Agent, or Firm*—Fisher, Christen & Sabol

(57) ABSTRACT

A process for preparing solid formulations of sodium 3-hydroxy-3-methylbutyrate of the formula

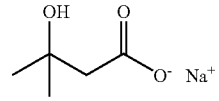

in which, in a first process step, 4,4-dimethyloxetan-2-one is reacted with aqueous sodium hydroxide to form a solution of sodium 3-hydroxy-3-methylbutyrate, and then, if appropriate after concentration, the solution is applied, in a further process step, to synthetic silica, and in which the resultant product is, if appropriate, dried.

19 Claims, No Drawings

METHOD FOR THE PRODUCTION OF SOLID FORMULATIONS OF SODIUM 3-HYDROXY-3-METHYLBUTYRATE

This application is a 371 national stage application of International (PCT) Application No. PCT/EP02/05435, filed on May 17, 2003 that has priority benefit of European Patent Application No. 01112236.3, filed on May 18, 2001.

The invention relates to a process for preparing solid formulations of the sodium salt of 3-hydroxy-3-methylbutyric acid (β-hydroxy-β-methylbutyric acid, HMB) of the formula

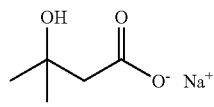

3-Hydroxy-3-methylbutyric acid is an active compound which is used as a medicament and food additive for humans and animals, for example for lowering blood cholesterol (WO-A-94/06417) or for decreasing nitrogen excretion, in particular in the case of ill and/or elderly humans (WO-A-94/14429). Customarily it is not the free acid which is used for this, but a physiologically acceptable salt, for example the calcium salt. For economic reasons, in particular for applications in animal nutrition or veterinary medicine, it would be desirable also to be able to use the sodium salt. Although this has been mentioned repeatedly in the literature, no industrial process for its preparation in solid form has been described and it has been found that it is not storage-stable and is hygroscopic and is therefore difficult to process.

It is an object of the present invention, therefore, to provide a simple and economic process for preparing a storage-stable solid (pulverulent) low-hygroscopic form of sodium 3-hydroxy-3-methylbutyrate.

This object is achieved according to the invention by the process as claimed in claim 1.

It has been found that a solution of sodium 3-hydroxy-3-methylbutyrate which is obtainable by hydrolyzing 4,4-dimethyloxetan-2-one with aqueous sodium hydroxide, if appropriate after concentration, by application to synthetic silica and, if appropriate, subsequent drying, can be brought into a low-hygroscopic, free-flowing and readily handleable form.

Suitable synthetic silicas are, in particular, the commercially conventional precipitated silicas as are obtainable commercially, for example, from Degussa under the name Sipernat®.

Preferably, the solution of sodium 3-hydroxy-3-methylbutyrate is brought to a concentration of at least 50% by weight, particularly preferably from 70 to 80% by weight, by distilling off water under reduced pressure. At the last-mentioned concentrations, the solution is expediently kept at a temperature of 60–65° C. to prevent crystallization. The concentration can be performed on a laboratory scale, for example in a conventional distillation apparatus, or on an industrial scale, for example in a thin-film evaporator. However, it is also possible to use directly the solutions occurring in the synthesis having contents of, for example, from 20 to 30% by weight.

Application of the solution of sodium 3-hydroxy-3-methylbutyrate can be performed in a conventional mixing apparatus, preferably for this a gentle mixer type is used, for example a drum mixer, plowshare mixer or cone mixer, a spray mixer or a (slow) intensive mixer. Too vigorous a mixing process can, surprisingly, lead to lump formation.

Preferably, the application is performed in such a manner that the synthetic silica is introduced first and the solution of sodium 3-hydroxy-3-methylbutyrate is added.

To decrease the water content in the finished product, the finished product can be dried in a manner known per se. However, even without drying, even at water contents of up to 30% by weight, products which are still free-flowing and outwardly dry are obtained.

For further improvement of the flowability, if appropriate, hydrophobic silicas (for example Sipernat® D17) or another flow improver can be added to the product prepared according to the invention. In this case, for example, amounts of from 0.2 to 0.4% by weight, based on the dry matter, of hydrophobic silica can be added towards the end of the mixing process and can be mixed in for a short time (for example 30 min).

The solid compositions obtainable by the inventive process, which compositions contain sodium 3-hydroxy-3-methylbutyrate and synthetic silica, are likewise subject-matter of the invention.

Preferably, the inventive compositions comprise at least 25% by weight of sodium 3-hydroxy-3-methylbutyrate, particularly preferably from 25 to 50% by weight, based on the dry matter.

The following examples illustrate the procedure of the invention without a restriction to be seen therein.

EXAMPLE 1

Preparation of a Solution of Sodium 3-hydroxy-3-methylbutyrate

A solution of sodium hydroxide (127.3 g; 3.15 mol) in water (1.5 l) was cooled to 0° C. Then, crude 4,4-dimethyloxetan-2-one (=β-isovalerolactone; 336.7 g; 3 mol; obtained by reacting ketene with acetone) was added dropwise in the course of approximately 2¼ h with vigorous stirring, with the temperature being kept from 1.5 to 2° C. The reaction mixture was stirred for a further 15 min at 0° C. and then heated for a further 40 min at 22° C. Then 415 g of water were distilled off at 300 mbar in the course of approximately 3 h. In this manner 1533 g of a solution containing approximately 27.5% by weight of sodium 3-hydroxy-3-methylbutyrate were obtained.

EXAMPLE 2

Preparation of the Solid Formulation

The solution of Example 1 was concentrated to 57.5% by weight at 50 mbar and 56° C. 50 g of synthetic silica (Sipernat® 50, Degussa AG) were charged in an Eirich intensive mixer (type R02). The disk rotation was set to stage 2 (the rotating blade head was out of operation) and 100 g of the solution were added in the course of 1 h via a tube. The mixing operation was then continued for a further ½ h. A homogeneous lump-free free-flowing and outwardly dry product was obtained.

What is claimed is:

1. A process for preparing a solid formulation of sodium 3-hydroxy-3-methylbutyrate of the formula:

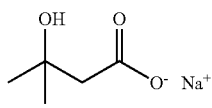

comprising (1) reacting 4,4-dimethyloxetan-2-one with aqueous sodium hydroxide to form a solution of sodium 3-hydroxy-3-methylbutyrate, (2) optionally concentrating said solution, (3) combining (i) said solution and (ii) synthetic silica, (4) obtaining a solid formation from the combination of (i) said solution and (ii) the synthetic silica, of sodium 3-hydroxy-3-methylbutyrate and synthetic silica, and (5) optionally drying the solid formulation of sodium 3-hydroxy-3-methylbutyrate and synthetic silica.

2. The process as claimed in claim 1, wherein the solution of sodium 3-hydroxy-3-methylbutyrate is concentrated under reduced pressure to a concentration of at least 50 percent by weight.

3. The process as claimed in claim 1, wherein said combining comprises applying said solution to said synthetic silica in a mixer selected from the group consisting of a drum mixer, a plowshare mixer, a cone mixer, and an intensive mixer.

4. The process as claimed in claim 1, wherein said combining is carried out by first introducing the synthetic silica into a mixer and then adding the solution of sodium 3-hydroxy-3-methylbutyrate thereto.

5. The process as claimed in claim 1, wherein an amount of hydrophobic silica sufficient to improve flowability of said formulation is also added during said combining.

6. A solid composition comprising sodium 3-hydroxy-3-methylbutyrate and synthetic silica, that has been prepared by the process according to claim 1.

7. The solid composition as claimed in claim 6, wherein the content of sodium 3-hydroxy-3-methylbutyrate, based on the dry matter, is at least 25 percent by weight.

8. The process as claimed in claim 2, wherein said combining comprising applying said solution to said synthetic silica is performed in a mixer selected from the group consisting of a drum mixer, a plowshare mixer, a cone mixer, and an intensive mixer.

9. The process as claimed in claim 2, wherein said combining is carried out by first introducing the synthetic silica into a mixer and then adding the solution of sodium 3-hydroxy-3-methylbutyrate thereto.

10. The process as claimed in claim 3, wherein said combining is carried out by first introducing the synthetic silica into the mixer and then adding the solution of sodium 3-hydroxy-3-methylbutyrate thereto.

11. The process as claimed in claim 2, wherein an amount of hydrophobic silica sufficient to improve flowability of said formulation is also added during said combining.

12. The process as claimed in claim 3, wherein an amount of hydrophobic silica sufficient to improve flowability of said formulation is also added during said combining.

13. The process as claimed in claim 4, wherein an amount of hydrophobic silica sufficient to improve flowability of said formulation is also added during said combining.

14. A solid composition comprising sodium 3-hydroxy-3-methylbutyrate and synthetic silica, that has been prepared by the process according to claim 2.

15. A solid composition comprising sodium 3-hydroxy-3-methylbutyrate and synthetic silica, that has been prepared by the process according to claim 3.

16. A solid composition comprising sodium 3-hydroxy-3-methylbutyrate and synthetic silica, that has been prepared by the process according to claim 4.

17. A solid composition comprising sodium 3-hydroxy-3-methylbutyrate and synthetic silica, that has been prepared by the process according to claim 5.

18. The solid composition as claimed in claim 7, wherein the content of sodium 3-hydroxy-3-methylbutyrate, based on the dry matter, is from about 25 to 50 percent by weight.

19. The process as claimed in claim 1, wherein the solution of sodium 3-hydroxy-3-methylbutyrate is concentrated under reduced pressure to a concentration of from 70 to 80 percent by weight.

* * * * *